United States Patent [19]

Fringeli

[11] 4,212,763
[45] Jul. 15, 1980

[54] BIS-TRIAZINYLAMINOSTILBENE COMPOUNDS AND THEIR USE AS FLUORESCENT BRIGHTENING AGENTS

[75] Inventor: Werner Fringeli, Laufen, Switzerland

[73] Assignee: Ciba-Geigy Corporation, Ardsley, N.Y.

[21] Appl. No.: 919,115

[22] Filed: Jun. 26, 1978

[30] Foreign Application Priority Data

Jul. 4, 1977 [CH] Switzerland .................. 8180/77

[51] Int. Cl.² .................. C07D 403/06; C07D 401/14
[52] U.S. Cl. .................. 252/301.23; 8/565; 162/162; 252/435; 427/158; 542/435; 542/461; 8/565
[58] Field of Search .............. 542/461, 435; 252/301.23, 453; 162/162; 427/158; 8/1 W

[56] References Cited

U.S. PATENT DOCUMENTS 2,846,397  8/1958  Ackermann .................. 542/461 X

FOREIGN PATENT DOCUMENTS

| | | | |
|---|---|---|---|
| 672539 | 11/1965 | Belgium | 542/461 |
| 1965585 | 7/1971 | Fed. Rep. of Germany | 542/461 |
| 2124079 | 12/1971 | Fed. Rep. of Germany | 542/461 |
| 286332 | 2/1953 | Switzerland | 542/461 |
| 1064618 | 4/1967 | United Kingdom . | |

*Primary Examiner*—Arthur P. Demers
*Attorney, Agent, or Firm*—Prabodh I. Almaula

[57] ABSTRACT

Bis-triazinylaminostilbene compounds of the formula

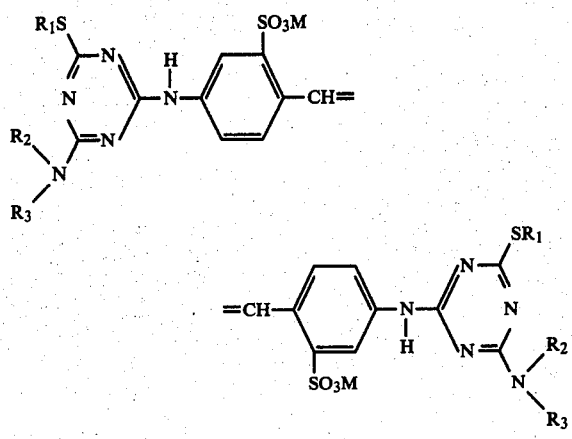

in which $R_1$ is alkyl, alkenyl, cyclohexyl or phenylalkyl, $R_2$ is hydrogen, alkyl, cyclohexyl, benzyl, alkyl which is substituted by hydroxyl, cyano, sulpho or carbamoyl, alkoxyalkyl or hydroxyalkoxyalkyl or alkoxyalkoxyalkyl or mono- or di-alkylaminoalkyl, and $R_3$ is hydrogen, alkyl, alkyl which is substituted by hydroxyl, cyano or sulpho, or alkoxyalkyl or hydroxyalkoxyalkyl or $R_2$ and $R_3$ together with the nitrogen atom to which they are bonded are a morpholine ring or a pyrrolidine, piperidine, hexamethyleneimine or piperazine ring which is unsubstituted or substituted by 1 or 2 alkyl groups, and M is hydrogen or an alkali metal, ammonium or amine ion, and, if $R_2$ or $R_3$ is hydroxyalkyl, $R_1$ is methyl, cyclohexyl or alkenyl only, and their use as fluorescent brightening agents for organic material of high molecular weight are disclosed.

21 Claims, No Drawings

BIS-TRIAZINYLAMINOSTILBENE COMPOUNDS AND THEIR USE AS FLUORESCENT BRIGHTENING AGENTS

The present invention relates to novel bis-triazinylaminostilbene compounds and their use as fluorescent brightening agents for organic material of high molecular weight, especially made of cellulose and polyamide.

Bis-triazinylaminostilbene compounds which are substituted by alkylthio or arylthio groups and fall under the general formula

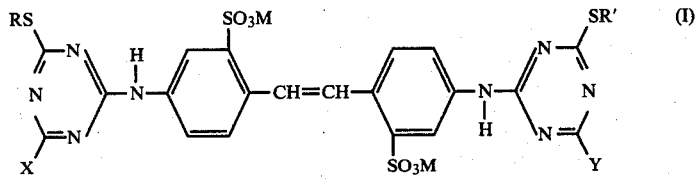

in which R and R' are substituted or unsubstituted alkyl or aryl groups, X and Y are substituted or unsubstituted amino groups and M is hydrogen or a salt-forming cation, are known from the literature (see U.S. Pat. No. 2,846,397 and British Pat. Nos. 1,064,618 and 1,296,080).

It has now been found, surprisingly, that a selected group of alkylthio-substituted bis-triazinylaminostilbene compounds has better properties than the similar compounds already known from the literature and these compounds are therefore more useful as fluorescent brightening agents.

The bis-triazinylaminostilbene compounds according to the invention are of the formula

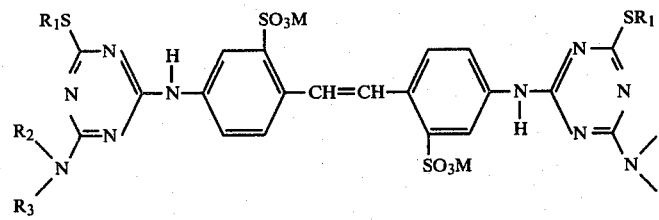

in which $R_1$ is alkyl having 1 to 6 carbon atoms, alkenyl having 3 or 4 carbon atoms, cyclohexyl or phenylalkyl having 1 to 4 carbon atoms in the alkyl moiety, $R_2$ is hydrogen, alkyl having 1 to 6 carbon atoms, cyclohexyl, benzyl, alkyl which is substituted by hydroxyl, cyano, sulpho or carbamoyl and has 1 to 4 carbon atoms in the alkyl moiety, alkoxyalkyl or hydroxyalkoxyalkyl each having a total of 2 to 6 carbon atoms or alkoxyalkoxyalkyl having a total of 4 to 6 carbon atoms or mono- or di-alkylaminoalkyl, each having 1 to 4 carbon atoms per alkyl moiety, and $R_3$ is hydrogen, alkyl having 1 to 6 carbon atoms, alkyl which has 1 to 4 carbon atoms and is substituted by hydroxyl, cyano or sulpho, or alkoxyalkyl or hydroxyalkoxyalkyl each having a total of 3 to 6 carbon atoms, or $R_2$ and $R_3$ together with the nitrogen atom to which they are bonded are a morpholine ring or a pyrrolidine, piperidine, hexamethyleneimine or piperazine ring which is unsubstituted or substituted by 1 or 2 alkyl groups having 1 to 4 carbon atoms, and M is hydrogen or an alkali metal, ammonium or amine ion, and, if $R_2$ or $R_3$ is hydroxyalkyl, $R_1$ is methyl, cyclohexyl or alkenyl only.

"Sulpho" is to be understood as meaning the group $-SO_3H$ and also salts thereof, in particular alkali metal salts, ammonium salts or amine salts thereof and especially the alkali metal salts thereof.

"Carbamoyl" has the formula $-CON<$ and the nitrogen atom can be substituted by 1 or 2 aliphatic or aromatic radicals but is preferably unsubstituted ($-CONH_2$).

Preferred compounds within the scope of the formula (1) are those of the formula

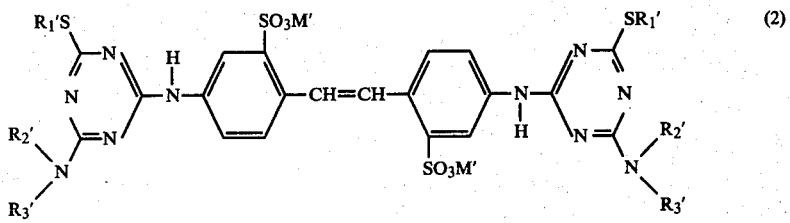

in which $R_1'$ is alkyl having 1 to 6 carbon atoms, $R_2'$ is hydrogen, alkyl having 1 to 6 carbon atoms, cyclohexyl, benzyl alkyl having 1 to 4 carbon atoms which is substituted by hydroxyl, sulpho or cyano, alkoxyalkyl having a total of 2 to 6 carbon atoms or mono- or dialkylaminoalkyl each having 1 to 4 carbon atoms per alkyl moiety and $R_3'$ is hydrogen, alkyl having 1 to 6 carbon atoms, alkyl having 1 to 4 carbon atoms which is substituted by hydroxyl or cyano, or alkoxyalkyl having a total of 3 to 6 carbon atoms, or $R_2'$ and $R_3'$ together with the nitrogen atom to which they are bonded are a pyrrolidine, piperidine, hexamethyleneimine, piperazine, N-methylpiperazine or morpholine ring, and M' is hydrogen or an alkali metal ion, and, if $R_2'$ or $R_3'$ is hydroxyalkyl, $R_1'$ is methyl only.

Compounds of particular interest are those of the formula

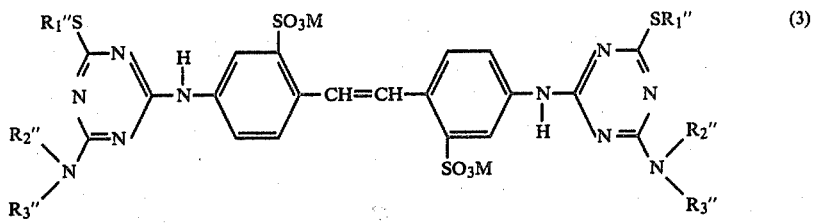

in which $R_1''$ is alkyl having 1 to 4 carbon atoms, alkenyl having 3 or 4 carbon atoms or cyclohexyl, $R_2''$ is hydrogen, alkyl having 1 to 4 carbon atoms, alkyl which is substituted by hydroxyl, cyano, sulpho or carbamoyl and has 2 to 4 carbon atoms in the alkyl moiety, alkoxyalkyl or hydroxyalkoxyalkyl each having a total of 3 to 6 carbon atoms or alkoxyalkoxyalkyl having a total of 4 to 6 carbon atoms or mono- or di-alkyl-aminoalkyl each having 1 to 4 carbon atoms per alkyl moiety and $R_3''$ is hydrogen, alkyl having 1 to 6 carbon atoms, alkyl having 2 to 4 carbon atoms which is substituted by hydroxyl, cyano or sulpho, or alkoxyalkyl or hydroxyalkoxyalkyl each having a total of 3 to 6 carbon atoms, or $R_2''$ and $R_3''$ together with the nitrogen atom to which they are bonded are a morpholine ring or a pyrrolidine, piperidine, hexamethyleneimine or piperazine ring which is unsubstituted or substituted by 1 or 2 alkyl groups, and M is hydrogen or an alkali metal, ammonium or amine ion, and, if $R_2''$ or $R_3''$ is hydroxyalkyl, $R_1''$ is methyl, alkenyl or cyclohexyl only, and also those of the formula

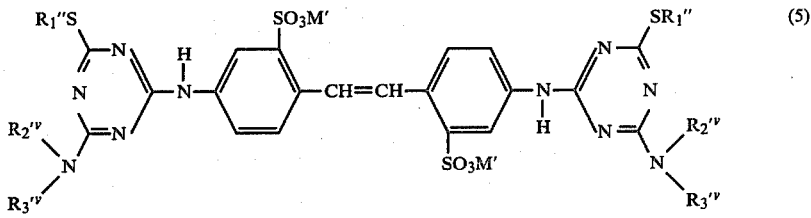

in which $R_1''$ is alkyl having 1 to 4 carbon atoms, $R_2'''$ is alkyl having 1 to 4 carbon atoms, alkyl having 2 to 4 carbon atoms which is substituted by hydroxyl, cyano, sulpho or carbamoyl, or alkoxyalkyl having 3 to 6 carbon atoms, and $R_3'''$ is hydrogen, alkyl having 1 to 4 carbon atoms, alkyl which is substituted by hydroxyl or cyano and has 2 to 4 carbon atoms in the alkyl moiety, or alkoxyalkyl having 3 to 6 carbon atoms, or $R_2'''$ and $R_3'''$ together with the nitrogen atom to which they are bonded are a morpholine ring or a pyrrolidine, piperidine, hexamethyleneimine or piperazine ring which is unsubstituted or substituted by 1 or 2 methyl groups, and M is hydrogen or an alkali metal, ammonium or amine ion, and, if $R_2'''$ or $R_3'''$ is hydroxyalkyl, $R_1''$ is methyl only.

Preferred compounds are those of the formula

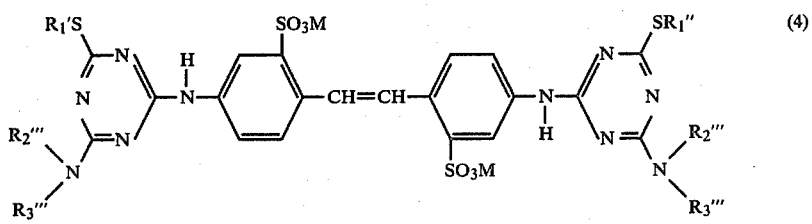

in which $R_1''$ is alkyl having 1 to 4 carbon atoms, $R_2^{iv}$ is alkyl having 1 to 4 carbon atoms, alkyl having 2 to 4 carbon atoms which is substituted by hydroxyl, cyano or carbamoyl, or alkoxyalkyl having 3 to 6 carbon atoms and $R_3^{iv}$ is hydrogen, alkyl having 1 to 4 carbon atoms, hydroxyalkyl having 2 to 4 carbon atoms or alkoxyalkyl having 3 to 6 carbon atoms, or $R_2^{iv}$ and $R_3^{iv}$ together with the nitrogen atom to which they are bonded are a pyrrolidine, piperidine, hexamethyleneimine or morpholine ring, and M' is hydrogen or an alkali metal ion, and, if $R_2^{iv}$ or $R_3^{iv}$ is hydroxyalkyl, $R_1''$ is methyl only.

Compounds distinguished by particularly good effects are those of the formulae

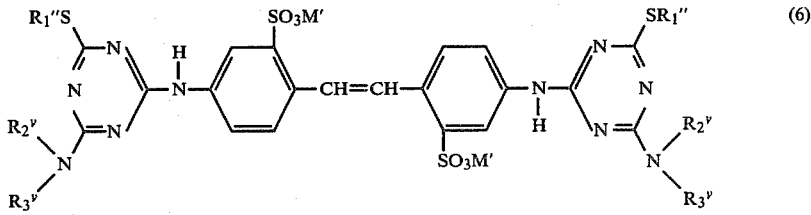

in which $R_1''$ is alkyl having 1 to 4 carbon atoms, $R_2^v$ is alkyl having 1 to 4 carbon atoms, cyanoalkyl having 1 to 4 carbon atoms in the alkyl moiety or alkoxyalkyl having a total of 2 to 6 carbon atoms and $R_3^v$ is hydrogen or alkyl having 1 to 4 carbon atoms, or $R_2^v$ and $R_3^v$ together with the nitrogen atom to which they are bonded are a piperidine, piperazine, N-methylpiperazine or morpholine ring, and M' is hydrogen or an alkali metal ion,

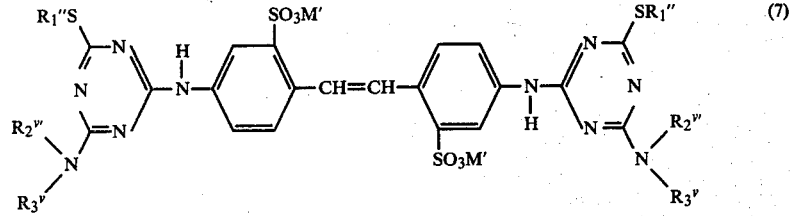

in which $R_1''$ is alkyl having 1 to 4 carbon atoms, $R_2^{vi}$ is alkyl having 1 to 4 carbon atoms and $R_3^v$ is hydrogen or alkyl having 1 to 4 carbon atoms, or $R_2^{vi}$ and $R_3^v$ together with the nitrogen atom to which they are bonded are a morpholine ring, and M' is hydrogen or an alkali metal ion, and

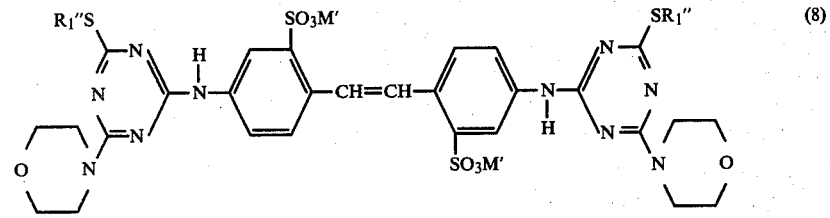

in which $R_1''$ is alkyl having 1 to 4 carbon atoms and M' is hydrogen or an alkali metal ion.

Compounds which are particularly important in practice are those bis-triazinylaminostilbene compounds of the formulae (1) to (8) in which the substituent $R_1$, $R_1'$ or $R_1''$ is methyl.

Very particularly preferred compounds are those of the formula

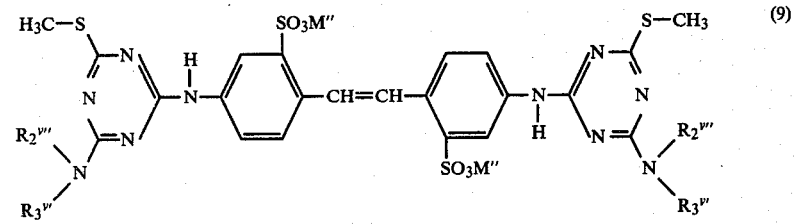

in which $R_2^{vii}$ is alkyl having 1 to 4 carbon atoms, hydroxyalkyl having 2 to 3 carbon atoms or alkoxyalkyl having 3 to 4 carbon atoms and $R_3^{vi}$ is hydrogen, alkyl having 1 to 4 carbon atoms, hydroxyalkyl having 2 to 3 carbon atoms or alkoxyalkyl having 3 to 4 carbon atoms, or $R_2^{vii}$ and $R_3^{vi}$ together with the nitrogen atom to which they are bonded are a morpholine ring, and M'' is hydrogen, sodium or potassium, and especially those in which the group $-N(R_2^{vii})(R_3^{vi})$ has the following meanings: morpholino, diethanolamino, diethylamino, $-NH(CH_2CH_2OCH_3)$ or $-N(CH_3)(CH_2CH_2OH)$.

The novel compounds of the formula (1) can be prepared by a novel improved process for the preparation of bis-triazinylaminostilbene compounds substituted by alkylthio.

Processes for the preparation of alkylthio-substituted bis-triazinylaminostilbene compounds of the formula (I) indicated initially are known, for example, from U.S. Pat. No. 2,846,397 and from British Patent Nos. 1,064,618 and 1,296,080.

In all of the processes known from the literature unsubstituted cyanuric chloride is used as the starting material and is reacted with a diaminostilbene and the reaction product is allowed to react with the corresponding amine and then with an alkyl- or aryl-mercaptan; the last two stages can also be carried out in reverse order, i.e. first the reaction with the mercaptan and then the reaction with the amine. It has also been described that cyanuric chloride can be reacted first with a corresponding amine, then with the diaminostilbene and in the final stage with a mercaptan. All of these processes, which have been described, have the disadvantage that they result in not very pure products, which has an adverse effect on the fluorescent brightener properties of the resulting compounds. The end products also usually have an unpleasant odour, caused by traces of mercaptans which are still present. Since the second and, in particular, the third process stage are carried out at relatively high temperatures, the reaction with short-chain alkylmercaptans, which have very low boiling points, is exceptionally difficult and it is for this reason that bis-triazinylaminostilbene compounds which are substituted by alkylthio groups having 1 to 3 carbon atoms have also hardly been described in the literature.

The compounds of the formula (1) can be prepared by a process which surprisingly does not have the above-mentioned disadvantages. This process comprises reacting one mol equivalent of a diaminostilbene of the formula

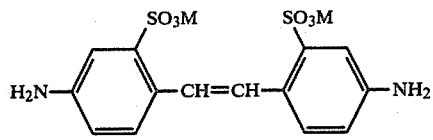

(10)

in the presence of an acid-binding agent with 2 mol equivalents of a compound of the formula

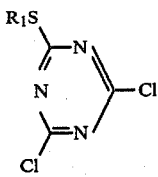

(11)

and reacting the resulting reaction product, after it has been isolated or without isolation, with 2 mol equivalents of an amine of the formula $HN(R_2)(R_3)$, in which M, $R_1$, $R_2$ and $R_3$ are as defined in formula (1).

The reaction medium used in preferably water, water-miscible organic solvents or mixtures of water and such solvents. The starting materials can be soluble in the solvent system used but can also form a dispersion with this system.

Examples of water-miscible organic solvents are: aliphatic ketones, such as acetone or methyl ethyl ketone, and water-soluble cyclic ethers, such as dioxane.

The two stages according to the invention can be carried out either in the same solvent system or in two different systems and are carried out in two different systems especially when the intermediate is isolated.

Advantageously, the reaction medium used is a mixture of water and an aliphatic ketone, preferably methyl ethyl ketone.

The reaction is preferably carried out in the presence of an emulsifier or of a mixture of several emulsifiers. For example, mixtures of anionic and non-ionic emulsifiers can be used for this purpose.

The first stage of the process according to the invention [reaction of compound (10) with compound (11)] is advantageously carried out at temperatures of 0° to 30° C., preferably at room temperature. The resulting intermediate of the formula

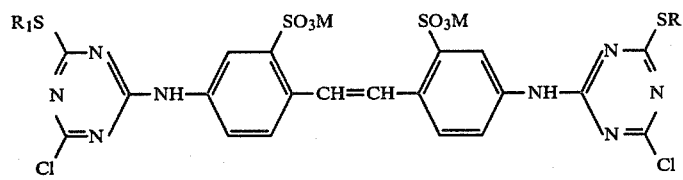

(12)

can be isolated, or the reaction with the amine can follow direct in the reaction mixture, without isolation of the intermediate. The second stage is preferably carried out at temperatures between 50° and 100° C. Although the reaction also proceeds at lower temperatures, for example 50° to 70° C., the reaction mixture is frequently heated to the reflux temperature of the particular solvent system used, in order to bring the reaction to completion.

The process is carried out in the presence of an acid-binding agent in order to neutralise the hydrochloric acid formed. Acid-binding agents are preferably alkali metal carbonates, hydroxides, bicarbonates and acetates, especially NaOH, $Na_2CO_3$ or $NaHCO_3$. However, organic bases, for example amines, especially tertiary or sterically hindered amines, can also be used. A base of this type, for example, triethylamine.

The same acid-binding agent can be used for both stages or a different acid-binding agent can be used for each of the two stages. Preferably, a solution of the acid-binding agent is added dropwise continuously in the course of the reaction, in order to maintain a constant pH value.

The reactants are employed in the molar ratios described above; only the amine can be added in a slight excess.

The starting materials of the formula (10) and also the amines required are known from the literature or can be obtained easily by methods known per se. The starting compounds of the formula (11) are also known or can be prepared by processes known per se, for example as described in Recueil des Travaux Chimiques des Pay-Bas 78 (1969) 967–980 (also see Example 1).

The bis-triazinylaminostilbene compounds, according to the invention, of the formula (1), which preferably are prepared by the novel process according to the invention, which has been described above, can in some cases also be prepared by the processes known from the literature (see above), although the preparation is then subject to the disadvantages described in these publications.

The novel bis-triazinylaminostilbene compounds, defined above, of the formula (1) and of the subsidiary formulae exhibit a more or less pronounced fluorescence in solution or dispersion. They can be used for the fluorescent brightening of a wide variety of synthetic, regenerated man-made or natural organic materials and this use is also a subject of the present invention.

Without any restriction being implied by the following classification, examples of organic materials which can undergo fluorescent brightening are:

I. Synthetic organic materials of high molecular weight:

(a) Polymerisation products based on organic compounds containing at least one polymerisable carbon-carbon double bond, i.e. their homopolymers or copolymers as well as their after-treatment products, for example crosslinking, grafting or degradation products, polymer blends, or products obtained by modification of reactive group, for example polymers based on α,β-unsaturated carboxylic acids or derivatives of such carboxylic acids, especially on acrylic compounds (for example acrylates, acrylic acid, acrylonitrile, acrylamides and their derivatives or their methacrylic analogues), on olefin hydrocarbons (for example ethylene, propylene, styrenes or dienes and also ABS polymers) and polymers based on vinyl and vinylidene compounds (for example vinyl chloride, vinyl alcohol and vinylidene chloride), (b) Polymerisation products which can be obtained by ring opening, for example polyamides of the polycaprolactam type, and also polymers which are obtainable either by polyaddition or by polycondensation, such as polyethers or polyacetals, (c) Polycondensation products or precondensates based on bifunctional or polyfunctional compounds with condensable groups, the homocondensation and co-condensation products, and after-treatment products thereof, for example polyesters, in particular saturated polyesters (for example polyesters of ethylene glycol terephthalic acid) or unsaturated polyesters (for example maleic acid/dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, the precondensates and analogues thereof, polycarbonates and silicones, (d) Polyaddition products, such as polyurethanes (crosslinked and uncrosslinked) and epoxide resins. II. Regenerated man-made organic materials, for example cellulose esters of varying degrees of esterification (so-called 2½-acetate or triacetate) or cellulose ethers, regenerated cellulose (viscose or cuprammonium cellulose), or their after-treatment products, and casein plastics. III. Natural organic materials of animal or vegetable origin, for example based on cellulose or proteins, such as cotton, wool, linen, silk, varnish gums, starch and casein.

The organic materials which are to undergo fluorescent brightening can be in the most diverse states of processing (raw materials, semi-finished goods or finished goods). On the other hand, they can be in the form of structures of the most diverse shapes, for example predominantly three-dimensionally expanded structures, such as sheets, profiles, injection mouldings, various machined articles, chips, granules or foams, and also predominantly two-dimensional structures, such as films, foils, lacquers, coverings, impregnations and coatings, or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

The novel compounds of the formulae (1) to (9) are especially suitable for the fluorescent brightening of organic material made of cellulose, wool and synthetic polyamide. The cellulose material can be either textile material (cotton) or paper. Synthetic polyamide is preferably whitened in the form of textile fibres.

Preferably, organic material of high molecular weight is whitened in the form of fibres. Advantageously, an aqueous dispersion of compounds, according to the invention, of the formula (1) is used for the fluorescent brightening of these fibrous materials. The fluorescent brightener dispersion preferably contains from 0.001 to 2%, and especially 0.05 to 1%, based on the fibrous material, of a stilbene derivative according to the invention. In addition, it can contain assistants, such as dispersing agents, for example condensation products of fatty alcohols containing 10 to 18 carbon atoms with 15 to 25 mols of ethylene oxide or condensation products of alkyl-mono- or -poly-amines containing 16 to 18 carbon atoms with at least 10 mols of ethylene oxide and, if desired, also acids, especially organic acids, such as acetic acid, oxalic acid and, preferably, formic acid.

The fluorescent brightening of the fibrous material with the aqueous fluorescent brightener dispersion is effected either by the exhaustion method at temperatures of, preferably, 60° to 100° C. or by the padding method.

The compounds according to the invention can also be used as fluorescent brightening agents for detergents, for examples of soaps, soluble salts of sulphuric acid hemiesters of higher fatty alcohols, arylsulphonic acids with higher and/or multiple alkyl substituents, sulphocarboxylic acid esters of medium to higher alkanols, higher alkanoylaminoalkyl- or -aminoaryl-carboxylic or -sulphonic acids or fatty acid glycerol sulphates; and also non-ionic detergents, such as higher alkylphenol polyglycol ethers.

Detergents according to the invention can contain the customary builders and assistants, for example alkali metal polyphosphates and polymetaphosphates, alkali metal silicates, alkali metal borates, alkali metal salts of carboxymethylcellulose, foam stabilisers, such as alkanolamides of higher fatty acids, or Complexons, such as soluble salts of ethylenediaminetetraacetic acid.

The novel stilbene derivatives are advantageously incorporated in the detergents, or in wash liquors, in the form of their solutions in neutral, water-miscible and/or readily volatile organic solvents, such as lower alkanols, lower alkoxyalkanols or lower aliphatic ketones. However, they can also be used in the finely divided solid form, on their own or as a mixture with dispersing agents. For example, they can be mixed, kneaded or ground with the detergents, and the conventional assistants and builders can then be mixed in. The fluorescent brightening agents are, for example, stirred to a slurry with the detergent substances, conventional assistants and builders and water and this slurry is then sprayed in a spray dried. The novel stilbene derivatives can also be admixed to finished detergents, for example by spraying a solution in a readily volatile and/or water-soluble organic solvent onto the dry detergents, which are kept in motion.

The content of fluorescent brightening agent of the formula (1) in the detergents is advantageously 0.001 to 0.5%, based on the solids content of the detergent. Compared with detergents which are free from fluorescent brightening agent, such detergents containing fluorescent brightening agents of the formula (1) impart a greatly improved white appearance in daylight. Wash liquors which contain compounds, according to the invention, of the formula (1) impart a brilliant appearance in daylight to textile fibres washed therewith. They can therefore be used, in particular, for washing these synthetic fibres or textiles consisting of such fibres, or constituents of textiles, and laundry. For use in household laundry they can also contain yet further fluorescent brightening agents which have an affinity for other fibres.

The novel stilbene derivatives of the formula (1) are also very suitable for the fluorescent brightening of paper.

For the fluorescent brightening of paper, the compounds according to the invention either can be added to the paper pulp or can be employed in surface finishing.

Surface coating methods are in general to be understood as meaning all operations relating to the finishing of a raw paper by coating it with a finishing agent.

Industrially, the surface finishing of paper is generally carried out by the following methods:

(A) In the so-called "starch coating" inside the paper machine, for example in a size press, or (B) In the so-called "pigment coating", inside or outside the paper machine.

For starch coating (surface sizing according to A), aqueous size liquors are used which in general contain 0.1 to 8 g per liter, for example 0.2 to 5 g per liter, of fluorescent brightening agents of the formula (1), 10 to 200 g/l, for example 20 to 150 g/l and preferably 50 to 100 g/l of binder and, if desired, a small amount of conventional wetting agents.

For pigment coating according to B), in general coating liquors are used which contain 0.1 to 8 g per liter, for example 0.2 to 6 g per liter, of fluorescent brightening agents of the formula (1), 50 to 700 g/l, for example 350 to 650 g/l, of white pigment and, if desired, based on the weight of the white pigment or pigments used, 8 to 30% of binder, 0.2 to 0.6% of metal-binding agents and 0.1 to 0.3% of wetting agents.

Binders are, for example, degraded starch, alginates, polyvinyl alcohol, polyvinylpyrrolidone, carboxymethylcellulose, proteins (for example gelatine and casein), aqueous dispersions of synthetic resins based on butadiene/styrene or acrylic polymers or copolymers, or mixtures of these binders.

Wetting agents are, for example, non-sulphated or sulphated higher alkanol polyglycol ethers or alkylphenol polyglycol ethers containing an alkyl radical having 8 to 14 C atoms and 1 to 20 ethylene oxide groups.

White pigments which can be used are, for example, aluminium magnesium silicates (china clay), calcium carbonate, $CaSO_4.1OH_2O$ (satin white), Al silicates and Al hydroxides, barium sulphate (blanc fix) or titanium dioxide, or mixtures of such white pigments. In addition, the coating liquors can contain metal-binding agents, for example, water-soluble polyphosphates or metal phosphates and salts of polycarboxylic acids, in order to eliminate undesired traces of metals (for example $Fe^{III}$).

In order to obtain a good flow properties, an alkaline coating liquor is adantageously used for pigment coating. The alkaline reaction is advantageously obtained using ammonium hydroxide or using sodium hydroxide, carbonate or borate or potassium hydroxide, carbonate or borate, or mixtures thereof.

Using these coating liquors according to A) and B), the paper is advantageously coated in a coating apparatus customary for this purpose. Papers are obtained which have, in addition to an improved surface and prinatability, a whiter and more pleasing appearance.

In the surface finishing process, the paper is coated in a known manner and aqueous solutions of the fluorescent brightening agents are added to size liquors or coating liquors which have already been prepared.

As a rule, aqueous 0.01 to 5%, preferably 0.05 to 2%, solutions of the fluorescent brightening agents are used.

In the following examples are by weight unless otherwise stated.

EXAMPLE 1

29.4 g of 2-methylthio-4,6-dichloro-1,3,5-triazine are finely dispersed in 500 ml of cold water. A solution of 36 g of the Na salt of 4,4'-diaminostilbene-2,2'-disulphonic acid in 160 ml of water is allowed to run into the resulting suspension in the course of 2 to 3 hours at 10° to 25° C. and the hydrochloric acid which is liberated is neutralised with a 15% sodium carbonate solution, so that the pH value of the mixture remains at 6.2 to 6.5

16 g of morpholine are now added to the reaction mixture and the resulting mixture is heated at 95° to 100° C. for 2 hours, the pH value of the reaction mixture being kept at 9.5 by adding a 15% sodium hydroxide solution. 140 g of sodium chloride are then added to the clear reaction solution and the product which has separated out is filtered off with suction at room temperature and dried in vacuo at 80° C. 56 g of the compound of the formula

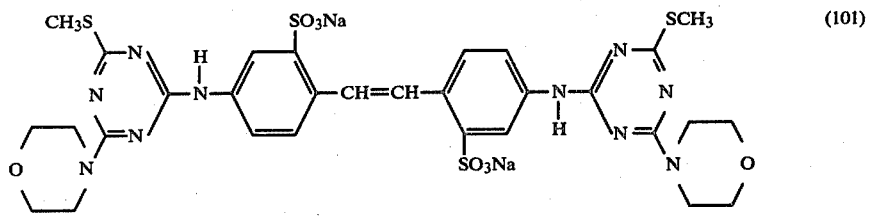

are obtained in the form of a yellow powder which is readily soluble in water.

$\lambda_{max} = 354$ nm $\epsilon = 44,000$ $FL_{max} = 432$ nm $Q = 0.58$ (in $DMF/H_2O$)

2-Methylthio-4,6-dichloro-1,3,5-triazine, which is used as the starting material, can be obtained, for example, as follows:

Methanethiol is passed into a solution of 18.5 g of cyanuric chloride in 200 ml of acetone at a temperature of −25° to −30° C. 13.5 ml of collidine are then added slowly at the same temperature, whereupon collidine hydrochloride precipitates. The mixture is left to stand for 1 hour at 0° C. and is then poured onto ice, whereupon a white crystalline substance precipitates. After filtering the mixture, washing the product with water and drying it in a desiccator, 17.5 g of 2-methylthio-4,6-dichloro-1,3,5-triazine with a melting point of 57° to 59° C. are obtained.

The methanethiol required is prepared by carefully heating 55.6 g of S-methylthiuronium sulphate with 80 ml of 5 N NaOH.

EXAMPLE 2

26.3 g of 2-ethylthio-4,6-dichloro-1,3,5-triazine are dissolved in 200 ml of methyl ethyl ketone and the solution is poured onto a mixture of 200 g of ice and 50 g of water, which contains 1 g of a mixture of a non-ionic emulsifier and an anionic emulsifier. A solution of 30.9 g of the Na salt of 4,4'-diaminostilbene-2,2'-disulphonic acid in 250 ml of water is allowed to run, in the course of one hour, at 10° to 25° C., into the suspension thus obtained and the hydrochloric acid which is liberated is neutralised with a 15% sodium carbonate solution so that the pH value of the mixture remains at 6.2 to 6.5. The mixture is stirred for a further one hour at 25°

EXAMPLE 4

The compounds of the formula

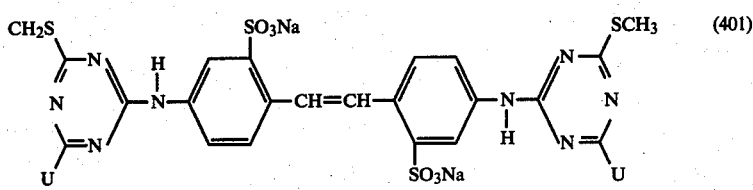

C., the pH value being maintained at 6.5. The disodium salt of 4,4'-bis-[4-chloro-6-ethylthio-1,3,5-triazin-2-yl-amino]-stilbene-2,2'-disulphonic acid which has precipitated is filtered off and washed once with 150 ml of water.

The moist disodium salt thus obtained is suspended in 750 ml of water and 13.5 of morpholine are added to the suspension. The mixture is then heated at 90° to 95° C. for 2 hours and the pH value is kept at 9.5 by adding a 15% sodium hydroxide solution. 100 g of sodium chloride are then added to the clear reaction solution and the product which has separated out is filtered off with suction at room temperature and dried in vacuo at 80° C. This yields 45 g of a yellow powder, which is readily soluble in water, of the compound of the formula listed in Table I below are obtained using the method indicated in Example 2 or 3 and replacing morpholine by the corresponding amounts of the particular amine.

TABLE I

| Formula No. | U |
|---|---|
| (402) | —N(CH₂CH₂OH)₂ |
| (403) | —NH—CH₂CH₂OH |
| (404) | —N(CH₃)—CH₂CH₂OH |
| (405) | —N(C₂H₅)₂ |
| (406) | —HN—CH₂CH₂—OCH₃ |
| (407) | —HN(CH₂)₃OCH₃ |
| (408) | —N(CH₂CH₂CN)(CH₂CH₂OCH₃) |
| (409) | —N(CH₂CH₂CONH₂)(CH₂CH₂OCH₃) |
| (410) | —N(piperidinyl) |
| (411) | —N(hexahydroazepinyl) |
| (412) | —N(heptamethyleneimino) |

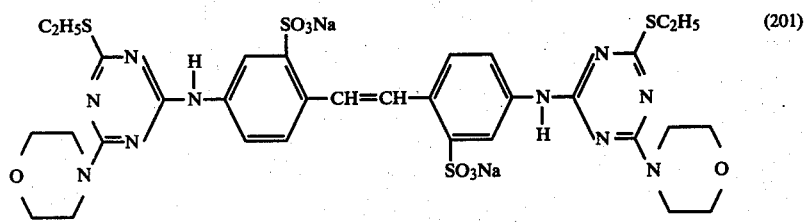

EXAMPLE 3

19.6 g of 2-methylthio-4,6-dichloro-1,3,5-triazine are dissolved in 150 ml of methyl ethyl ketone and the solution is poured onto a mixture of 100 g of ice and 100 g of water, which contains 0.3 g of a conventional emulsifier. A solution of 25.5 g of the Na salt of 4,4'-diaminostilbene-2,2'-disulphonic acid in 200 ml of water is allowed to run, in the course of one hour, at 10° to 25° C., into the suspension thus obtained and the hydrochloric acid which is liberated is neutralised with a 15% sodium carbonate solution so that the pH value of the mixture remains at 6.2 to 6.5. The mixture is stirred for a further one hour at 25° C., a pH value of 6.5 being maintained. 10.5 g of morpholine are now added to the reaction mixture and the resulting mixture is heated for three hours at 75° to 80° C., the pH value of the reaction mixture being kept at 9.5 by adding a 15% sodium hydroxide solution. 25 g of sodium chloride are then added to the clear reaction solution and the product which has separated out is filtered off with suction at room temperature and dried in vacuo at 80° C. 36.4 g of the compound of the formula (101) are obtained in the form of a yellow powder which is readily soluble in water.

EXAMPLE 5

The compounds of the formula

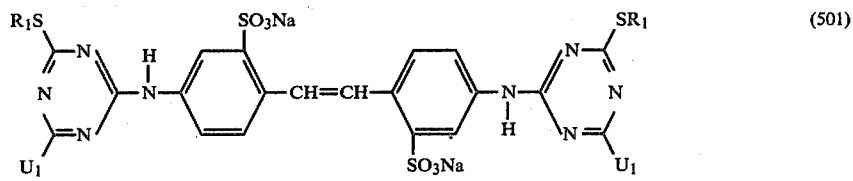
(501)

listed in Table II below are obtained using the method indicated in Example 2 or 3 and replacing 2-methylthio- (or 2-ethylthio-)-4,6-dichloro-1,3,5-triazine or/and morpholine by the corresponding amounts of 2-alkylthio-4,6-dichloro-1,3,5-triazine or/and the particular amine.

TABLE II

| Formula No. | $R_1$ | $U_1$ |
| --- | --- | --- |
| (502) | n-$C_3H_7$— | —N(morpholine) |
| (503) | n-$C_4H_9$— | —N(morpholine) |
| (504) | n-$C_4H_9$— | —N($CH_2CH_2OH$)$_2$ |
| (505) | $CH_3$— | —N($CH_2$—CH(OH)—$CH_3$)$_2$ |
| (506) | n-$C_4H_9$— | —N($CH_3$)$CH_2CH_2OH$ |
| (507) | n-$C_4H_9$— | —N($C_2H_5$)$_2$ |
| (508) | n-$C_4H_9$— | —HN—$CH_2CH_2$—$OCH_3$ |
| (509) | $CH_3$— | —N($CH_3$)$CH_2CH_2CN$ |
| (510) | $CH_3$— | —$NH_2$ |
| (511) | n-$C_4H_9$— | —$NH_2$ |
| (512) | $CH_3$— | —HN—($CH_2$)$_3$O($CH_2$)$_3$—OH |
| (513) | $CH_3$— | —HN—$CH_2CH_2SO_3H$ |
| (514) | $CH_3$— | —N($CH_3$)$CH_2CH_2SO_3H$ |
| (515) | $CH_3$— | —N(piperazine)N—$CH_3$ |
| (516) | —CH($CH_3$)$_2$ | —N(morpholine) |
| (517) | —CHCH$_2$CH$_3$ / $CH_3$ | —N(morpholine) |
| (518) | —$CH_2CHCH_3$ / $CH_3$ | —N(morpholine) |
| (519) | —C($CH_3$)$_3$ | —N(morpholine) |
| (520) | —($CH_2$)$_4CH_3$ | —N(morpholine) |
| (521) | —$CH_2CH_2CHCH_3$ / $CH_3$ | —N(morpholine) |
| (522) | —$C_2H_5$ | —N($CH_2CH_2OH$)$_2$ |
| (523) | -n-$C_3H_7$ | —N($CH_2CH_2OH$)$_2$ |
| (524) | —$C_2H_5$ | —N($CH_2CHCH_3$)$_2$ / OH |
| (525) | -n-$C_3H_7$ | —N($CH_2CHCH_3$)$_2$ / OH |
| (526) | -n-$C_4H_9$ | —N($CH_2CHCH_3$)$_2$ / OH |
| (527) | —$C_2H_5$ | —N($C_2H_5$)$_2$ |
| (528) | -n-$C_3H_7$ | —N($C_2H_5$)$_2$ |
| (529) | —$CH_3$ | —$NHC_2H_5$ |
| (530) | —$CH_3$ | —$NHCH_3$ |
| (531) | —$CH_3$ | —N(piperazine)N—$CH_3$ |
| (532) | —$CH_3$ | —N(piperazine)N—$CH_2CH_2OH$ |
| (533) | —$C_2H_5$ | —$NHCH_2CH_2SO_3H$ |
| (534) | -n-$C_4H_9$ | —$NHCH_2CH_2SO_3H$ |
| (535) | —$C_2H_5$ | —N($CH_3$)$CH_2CH_2SO_3H$ |
| (536) | -n-$C_4H_9$ | —N($CH_3$)$CH_2CH_2SO_3H$ |
| (537) | —$CH_3$ | —N($CH_2CH_2CN$)$_2$ |
| (538) | —$CH_2CH=CH_2$ | —N($CH_2CH_2OH$)$_2$ |
| (539) | —$CH_2CH=CH_2$ | —N(morpholine) |

EXAMPLE 6

A piece of cotton fabric is padded at room temperature with a liquor of the following composition: 2 g of a fluorescent brightening agent of the formula (101), (403) or (404) and 1,000 ml of softened water.

The liquor pick-up is about 70%.

The fabric is then dried at 130° C. for 30 seconds. It then has a strong white effect.

EXAMPLE 7

A piece of polyamide 6 woven tricot is padded at room temperature with a liquor of the following composition: 2 g of a fluorescent brightening agent of the formula (101), (403), (405) or (406), 2 g of ®Calgon T, 15 ml of ®Polydiol 600, 5 ml of 80% acetic acid and 980 ml of softened water.

The liquor pick-up is about 100%.

The substrate is then dried and thermofixed at 190° C. for 40 seconds. The fabric then has a strong white effect.

EXAMPLE 8

0.06 ml of 40% acetic acid and 0.36 g of sodium bisulphite stabilised with sodium phosphate are added to 110 ml of water.

A solution of a fluorescent brightening agent of the formula (101) is prepared by dissolving 1 g in 1,000 ml of water. 7.5 ml of this stock solution are added to the solution described above. This aqueous solution containing the fluorescent brightening agent is warmed to 40° C. and wool fabric or yarn weighing 3 g is then put into the solution. The temperature is raised to 60° C. in the course of 10 to 15 minutes and this temperature is maintained for 60 minutes. The fabric is then rinsed in running cold water for 2 minutes and then dried for 20 minutes at 60° C.

The fabric treated in this way has a distinct white effect with very good fastness to light.

Similarly good effects are obtained when the fluorescent brightening agent of the formula (101) is replaced by a fluorescent brightening apart of the formula (402), (403), (404) or (409).

EXAMPLE 9

0.2 of Glauber's salt is added to 100 ml of water. A solution of a fluorescent brightening agent of the formula (101), (402), (404) or (405) is prepared by dissolving 1 g in 1,000 ml of water. 2 ml of this stock solution are added to the solution described above. This aqueous solution containing the fluorescent brightening agent is warmed to 40° to 45° C. Pre-bleached cotton fabric weighing 3 is then put in the solution and treated at this temperature for 30 minutes. The fabric is then rinsed in running cold water for 2 minutes and then dried for 20 minutes at 60° C.

The fabric treated in this way has a distinct white effect.

EXAMPLE 10

0.4 g of detergent is added to 100 ml of water, the detergent having the following composition: 16% of dodecyl benzenesulphonate, 4% of a fatty alcohol sulphonate, 35% of Na tripolyphosphate, 7% of tetra-Na pyrophosphate, 2% of Mg silicate ($MgSiO_3$), 7% of Na disilicate ($Na_2(SiO_3)_2$), 1% of carboxymethylcellulose, 0.5% of ethylenediaminetetraacetic acid (Na salt), *about 25% of Glauber's salt and 2.5% of water.

*(The detergent can also contain 10 to 20% of Na perborate or another oxygen donor in place of Glauber's salt).

A solution of the fluorescent brightening agent of the formula (101) is prepared by dissolving 1 g in 1,000 ml of water. 2 ml of this stock solution are added to the solution described above. This aqueous solution containing the fluorescent brightening agent is warmed to 60° C. Prebleached cotton fabric weighing 3 g is then put into the solution. The temperature is raised to 92° C. in the course of 10 to 15 minutes and this temperature is maintained for 30 minutes. The fabric is then rinsed in running cold water for 2 minutes and then dried for 20 minutes at 60° C. The fabric treated in this way has a distinct white effect.

Similarly good effects are obtained when the fluorescent brightening agent of the formula (101) is replaced by a fluorescent brightening agent of the formula (402), (404) or (405).

EXAMPLE 11

0.06 g of octadecyl polyglycol ether is added to 100 ml of water. A solution of a fluorescent brightening agent of the formula (101), (402), (404), (405), (406) or (407) is prepared by dissolving 1 g in 1,000 ml of water. 3 ml of this stock solution are added to the solution described above. This aqueous solution containing the fluorescent brightening agent is warmed to 60° C. and a nylon fabric weighing 3 g is then put into the solution. The temperature is raised to 92° to 95° C. in the course of 10 to 15 minutes and this temperature is maintained for 30 minutes. The fabric is then rinsed in running cold water for 2 minutes and then dried for 20 minutes at 60° C. The fabric treated in this way has a distinct white effect.

EXAMPLE 12

0.12 ml of 85% formic acid is added to 100 of water. A solution of a fluorescent brightening agent of the formula (101), (402), (403), (406) or (407) is prepared by dissolving 1 g in 1,000 ml of water. 3 ml of this stock solution are added to the solution described above. This aqueous solution containing the fluorescent brightening agent is warmed to 60° C. and a polyamide fabric weighing 3 is then put into the solution. The temperature is raised to 92° 95° C. in the course of 10 to 15 minutes and this temperature is maintained for 30 minutes. The fabric is then rinsed in running cold water for 2 minutes and then dried for 20 minutes at 60° C. The fabric treated in this way has a distinct white effect.

EXAMPLE 13

0.9 g of sodium bisulphite stabilised with sodium phosphate, 0.6 g of nonylphenyl polyglycol ether/fatty acid amide and 0.15 g of the sodium salt of ethylenediaminetetraacetic acid and also 0.6 ml of 40% acetic acid are added to 290 ml of water. A solution of the fluorescent brightening agent of the formula (101) is prepared by dissolving 1 g in 1,000 ml of water. 10 ml of this stock solution are added to the solution described above. This aqueous solution containing the fluorescent brightening agent is warmed to 60° C. A nylon fabric weighing 15 g is then put into the solution. The temperature is raised to 120° C. in the course of 15 to 20 minutes and this temperature is maintained for 30 minutes. The bath is then cooled to 60° C. in the course of 10 to 15 minutes. The fabric is then rinsed in running cold water for 2 minutes and then dried for 20 minutes at 60° C. The fabric treated in this way has a distinct white effect.

EXAMPLE 14

0.36 g of Na bisulphite stabilised with Na phosphate are added to 110 ml of water. A solution of a fluorescent brightening agent of the formula (101) is prepared by dissolving 1 g in 1,000 ml of water. 7.5 ml of this stock solution are added to the solution described above. This aqueous solution containing the fluorescent brightening agent is warmed to 40° C. and a pre-bleached wool fabric or yarn weighing 3 g is then put into the solution. The temperature is raised to 60° C. in the course of 10 to 15 minutes and this temperature is maintained for 60 minutes. The fabric is then rinsed in running cold water for 2 minutes and then dried for 20 minutes at 60° C. The fabric treated in this way has a distinct white effect.

EXAMPLE 15

An aqueous suspension of 100 parts of cellulose in 4,000 parts of water is mixed with an aqueous solution of 0.1 part of the fluorescent brightening agent of the formula (101) for 15 minutes in a hollander, two parts of resin milk and 3 parts of aluminium sulphate are added and the mixture is diluted with 20,000 parts of backwater, which contains 1 g of aluminium sulphate per liter, and processed in the customary manner to paper sheets. The resulting paper sheets have a distinct white effect.

EXAMPLE 16

In order to produce a paper charged with white pigment, 0.10 part of the fluorescent brightening agent of the formula (101) is added to an aqueous suspension containing 85 parts of cellulose and 15 parts of an aluminium silicate white pigment having the tradename "China Clay" and the suspension is processed in the conventional manner with 2 parts of resin milk and 4 parts of aluminium sulphate to give a paper structure. A charged paper with a white appearance is thus obtained.

EXAMPLE 17

A pigment coating liquor of the following composition is prepared: 150 ml of a 50% aqueous synthetic resin dispersion based on a crosslinkable methyl acrylate/methyl methacrylate/styrene copolymer (for example ACRONAL S 320 D ® from BASF), 100 ml of water containing 2 g of sodium polyphosphate, 600 ml of water containing 4 g of the fluorescent brightening agent of the formula (101), 50 ml of water containing 2 g of nonylphenol pentadecyl glycol ether and 500 g of aluminium magnesium silicate (China Clay Dinkie A).

A sized and charged sulphite cellulose raw paper is coated with this treatment liquor and then dried. A brilliant white paper with good printability is obtained.

What is claimed is:

1. A bis-triazinylaminostilbene compound, of the formula

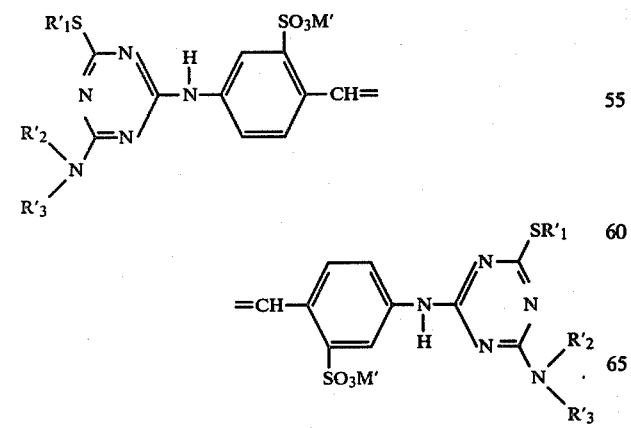

in which $R_1'$ is alkyl having 1 to 6 carbon atoms, $R_2'$ is hydrogen, alkyl having 1 to 6 carbon atoms, cyclohexyl, benzyl, alkyl having 1 to 4 carbon atoms which is substituted by hydroxyl, sulpho or cyano, alkoxyalkyl having a total of 2 to 6 carbon atoms or mono- or dialkylaminoalkyl each having 1 to 4 carbon atoms per alkyl moiety and $R_3'$ is hydrogen, alkyl having 1 to 6 carbon atoms, alkyl having 1 to 4 carbon atoms which is substituted by hydroxyl or cyano, or alkoxyalkyl having a total of 3 to 6 carbon atoms, or $R_2'$ and $R_3'$ together with the nitrogen atom to which they are bonded are a pyrrolidine, piperidine, hexamethyleneimine, piperazine, N-methylpiperazine or morpholine ring, and M' is hydrogen or an alkali metal ion, and, if $R_2'$ or $R_3'$ is hydroxyalkyl, $R_1'$ is methyl only.

2. A bis-triazinylaminostilbene compound according to claim 1, of the formula

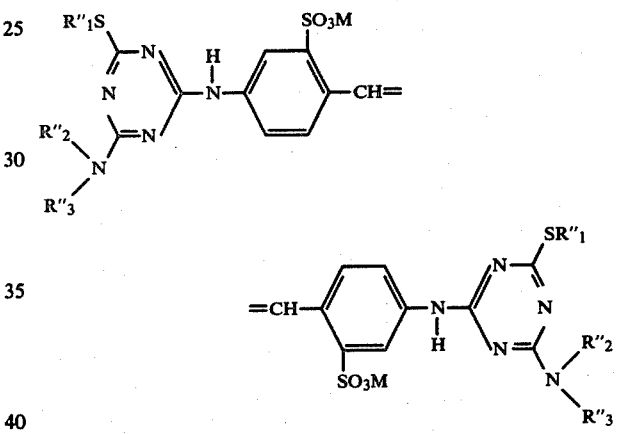

in which $R_1''$ is alkyl having 1 to 4 carbon atoms, alkenyl having 3 or 4 carbon atoms or cyclohexyl, $R_2''$ is hydrogen, alkyl having 1 to 4 carbon atoms, alkyl which is substituted by hydroxyl, cyano, sulpho or carbamoyl and has 2 to 4 carbon atoms in the alkyl moiety, alkoxyalkyl or hydroxyalkoxyalkyl each having a total of 3 to 6 carbon atoms or alkoxyalkoxyalkyl having a total of 4 to 6 carbon atoms or mono- or dialkylaminoalkyl each having 1 to 4 carbon atoms per alkyl moiety and $R_3''$ is hydrogen, alkyl having 1 to 6 carbon atoms, alkyl having 2 to 4 carbon atoms which is substituted by hydroxyl, cyano or sulpho, or alkoxyalkyl or hydroxyalkoxyalkyl each having a total of 3 to 6 carbon atoms, or $R_2''$ and $R_3''$ together with the nitrogen atom to which they are bonded are a morpholine ring or a pyrrolidine, piperidine, hexamethyleneimine or piperazine ring, and M is hydrogen or an alkali metal, ammonium or amine ion, and, if $R_2''$ or $R_3''$ is hydroxyalkyl, $R_1''$ is methyl, only.

3. A bis-triazinylaminostilbene compound according to claim 2, of the formula

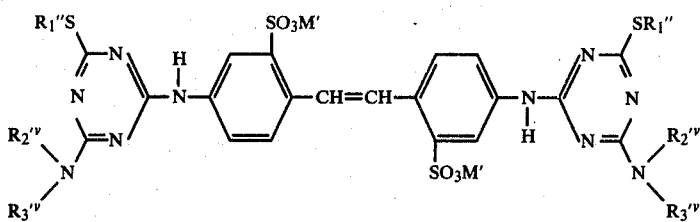

in which $R_1''$ is alkyl having 1 to 4 carbon atoms, $R_2'^v$ is alkyl having 1 to 4 carbon atoms, alkyl having 2 to 4 carbon atoms which is substituted by hydroxyl, cyano or carbamoyl, or alkoxyalkyl having 3 to 6 carbon atoms and $R_3'^v$ is hydrogen, alkyl having 1 to 4 carbon atoms, hydroxyalkyl having 2 to 4 carbon atoms or alkoxyalkyl having 3 to 6 carbon atoms, or $R_2'^v$ and $R_3'^v$ together with the nitrogen atom to which they are bonded are a pyrrolidine, piperidine, hexamethyleneimine or morpholine ring, and M' is hydrogen or an alkali metal ion, and, if $R_2'^v$ or $R_3'^v$ is hydroxyalkyl, $R_1'$ is methyl only.

4. A bis-triazinylaminostilbene compound according to claim 1, of the formula

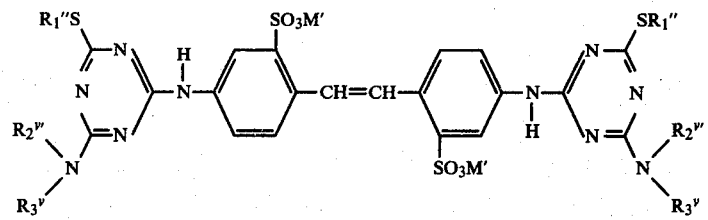

in which $R_1''$ is alkyl having 1 to 4 carbon atoms, $R_2'^v$ is alkyl having 1 to 4 carbon atoms, cyanoalkyl having 1 to 4 carbon atoms in the alkyl moiety or alkoxyalkyl having a total of 2 to 6 carbon atoms and $R_3'^v$ is hydrogen or alkyl having 1 to 4 carbon atoms, or $R_2'^v$ and $R_3'^v$ together with the nitrogen atom to which they are bonded are a piperidine, piperazine, N-methylpiperazine or morpholine ring, and M' is hydrogen or an alkali metal ion.

5. A bis-triazinylaminostilbene compound according to claim 4, of the formula

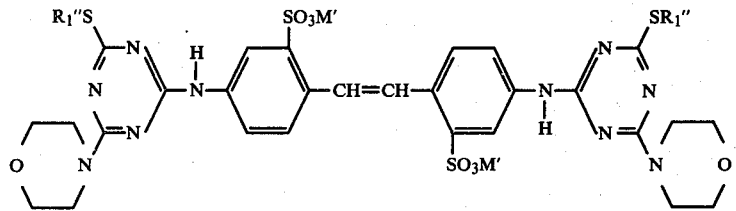

in which $R_1''$ is alkyl having 1 to 4 carbon atoms, $R_2^{v'}$ is alkyl having 1 to 4 carbon atoms and $R_3^v$ is hydrogen or alkyl having 1 to 4 carbon atoms, or $R_2^{v'}$ and $R_3^v$ together with the nitrogen atom to which they are bonded are a morpholine ring, and M' is hydrogen or an alkali metal ion.

6. A bis-triazinylaminostilbene compound according to claim 5, of the formula

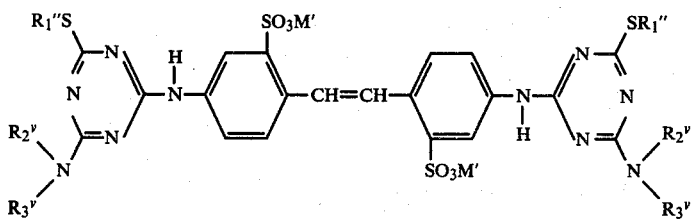

in which $R_1''$ is alkyl having 1 to 4 carbon atoms and M' is hydrogen or an alkali metal ion.

7. A bis-triazinylaminostilbene compound according to claim 2, of the formula

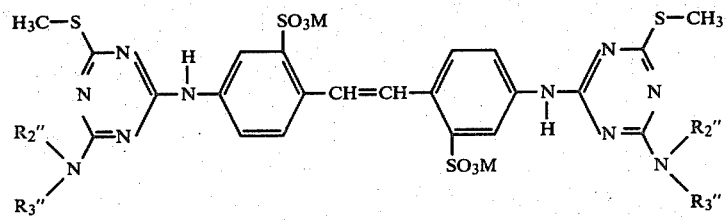

in which $R_2''$, $R_3''$ and M are as defined in claim 3.

8. A bis-triazinylaminostilbene compound according to claim 7, of the formula

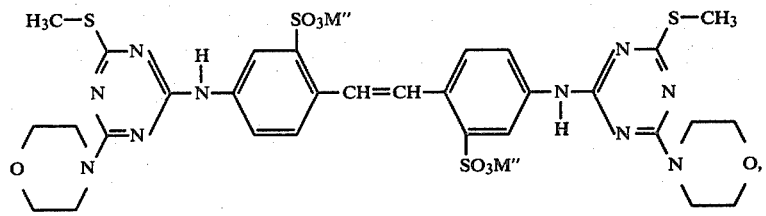

in which M'' is hydrogen, sodium or potassium.

9. A bis-triazinylaminostilbene compound according to claim 8, of the formula

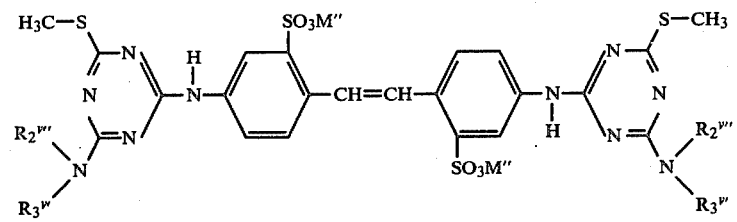

in which $R_2'''$ is alkyl having 1 to 4 carbon atoms, hydroxylalkyl having 2 to 3 carbon atoms or alkoxyalkyl having 3 to 4 carbon atoms and $R_3'''$ is hydrogen, alkyl having 1 to 4 carbon atoms, hydroxyalkyl having 2 to 3 carbon atoms or alkoxyalkyl having 3 to 4 carbon atoms, or $R_2'''$ and $R_3'''$ together with the nitrogen atom to which they are bonded are a morpholine ring, and M'' is hydrogen, sodium or potassium.

10. A bis-triazinylaminostilbene compound according to claim 2, of the formula

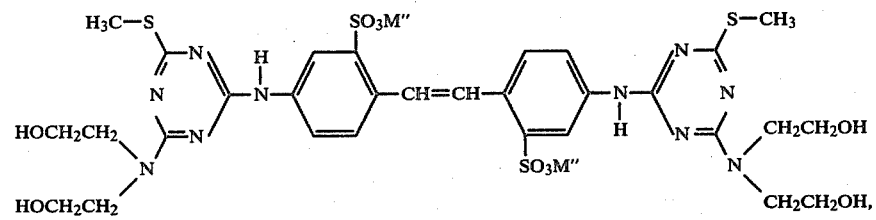

in which M'' is hydrogen, sodium or potassium.

11. A bis-triazinylaminostilbene compound according to claim 8, of the formula

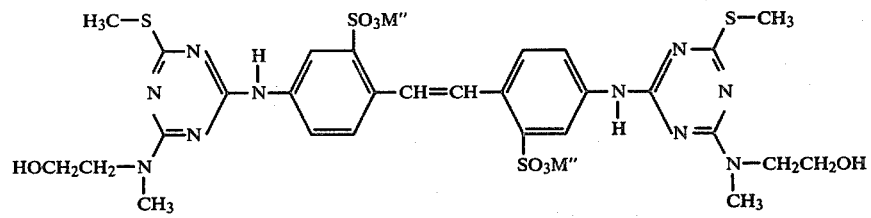

in which M'' is hydrogen, sodium or potassium.

12. A bis-triazinylaminostilbene compound according to claim 8, of the formula

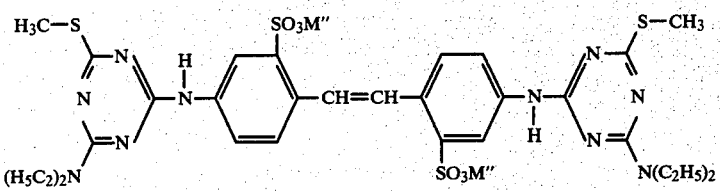

in which M″ is hydrogen, sodium or potassium.

13. A bis-triazinylaminostilbene compound according to claim 8, of the formula

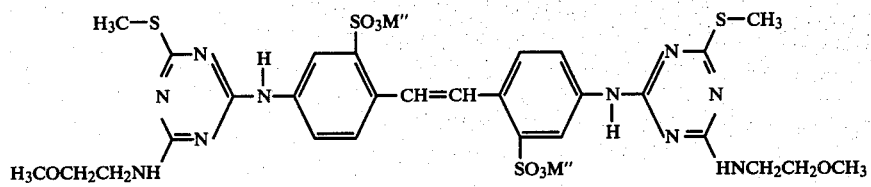

in which M″ is hydrogen, sodium or potassium.

14. A process for the fluorescent brightening of organic material of high molecular weight, which comprises incorporating a compound as defined in claim 1 into this material or applying such a compound to the surface of the said material.

15. A process according to claim 14, for the fluorescent brightening of material made of cellulose or polyamide.

16. A process according to claim 15, for the fluorescent brightening of textile material made of cellulose or polyamide.

17. A process according to claim 15, for the fluorescent brightening of paper, in the pulp or by surface coating.

18. A process according to claim 14, which comprises applying to the material to undergo fluorescent brightening, or incorporating into this material, 0.001 to 2%, preferably 0.01 to 0.5%, of the fluorescent brightening agent, based on the weight of the material to undergo fluorescent brightening.

19. Organic material containing 0.001 to 2, preferably 0.01 to 0.5, percent by weight of one or more of the compounds defined in claim 1.

20. A detergent containing, in addition to conventional detergent constituents, at least one bis-triazinylaminostilbene compound defined in claim 1.

21. A detergent according to claim 20, containing at least one organic detergent, at least one builder salt and 0.01 to 1% of a bis-triazinylaminostilbene compound.

* * * * *